(12) United States Patent
Baker et al.

(10) Patent No.: US 10,882,802 B2
(45) Date of Patent: Jan. 5, 2021

(54) PROCESS FOR CATALYTIC HYDRODEFLUORODIMERIZATION OF FLUOROÖLEFINS

(71) Applicant: UNIVERSITY OF OTTAWA, Ottawa (CA)

(72) Inventors: Ralph Thomas Baker, Ottawa (CA); Alexandre James Sicard, Ottawa (CA)

(73) Assignee: UNIVERSITY OF OTTAWA, Ontario (CA)

( * ) Notice: Subject to any disclaimer, the term of this patent is extended or adjusted under 35 U.S.C. 154(b) by 0 days.

(21) Appl. No.: 16/889,910

(22) Filed: Jun. 2, 2020

(65) Prior Publication Data

US 2020/0354295 A1    Nov. 12, 2020

Related U.S. Application Data

(62) Division of application No. 16/329,603, filed as application No. PCT/CA2017/051023 on Aug. 30, 2017, now Pat. No. 10,703,695.

(60) Provisional application No. 62/381,841, filed on Aug. 31, 2016.

(51) Int. Cl.
| | | |
|---|---|---|
| *C07C 17/278* | (2006.01) | |
| *B01J 31/22* | (2006.01) | |
| *C07C 21/18* | (2006.01) | |
| *C07F 15/04* | (2006.01) | |
| *C07C 17/23* | (2006.01) | |
| *C09K 5/04* | (2006.01) | |

(52) U.S. Cl.
CPC .......... *C07C 17/278* (2013.01); *B01J 31/2273* (2013.01); *C07C 17/23* (2013.01); *C07C 21/18* (2013.01); *C07F 15/04* (2013.01); *B01J 2231/44* (2013.01); *B01J 2531/847* (2013.01); *C09K 5/045* (2013.01)

(58) Field of Classification Search
CPC ....... C07C 17/728; C07C 17/23; C07C 21/18; C07F 15/04; B01J 31/2273; B01J 2531/847; B01J 2231/44; C09K 5/045
See application file for complete search history.

(56) References Cited

U.S. PATENT DOCUMENTS

2010/0154419 A1    6/2010  Kontomaris

OTHER PUBLICATIONS

Alexandre J. Sicard, "Organometallic Manipulations of Fluoroolefins Mediated or Catalyzed by Low-Coordinate Nickel", (M.Sc. Thesis), Published Online by the University of Ottawa, pp. 1-145 (Jun. 22, 2016).

*Primary Examiner* — Jafar F Parsa
(74) *Attorney, Agent, or Firm* — Hoffmann & Baron, LLP

(57) ABSTRACT

The present application provides a hydrodefluorodimerization process, which is useful in the synthesis of, for example, fluoroolefins that can be used as refrigerants, blowers and the like. The process is an "early-stage fluorination" process, wherein precursors containing fluorine are assembled into the desired product using a zerovalent nickel catalyst. Also provided is a liquid composition comprising one or more fluoroolefin produced by this catalytic process.

11 Claims, 2 Drawing Sheets

PROCESS FOR CATALYTIC HYDRODEFLUORODIMERIZATION OF FLUOROÖLEFINS

Figure 1:
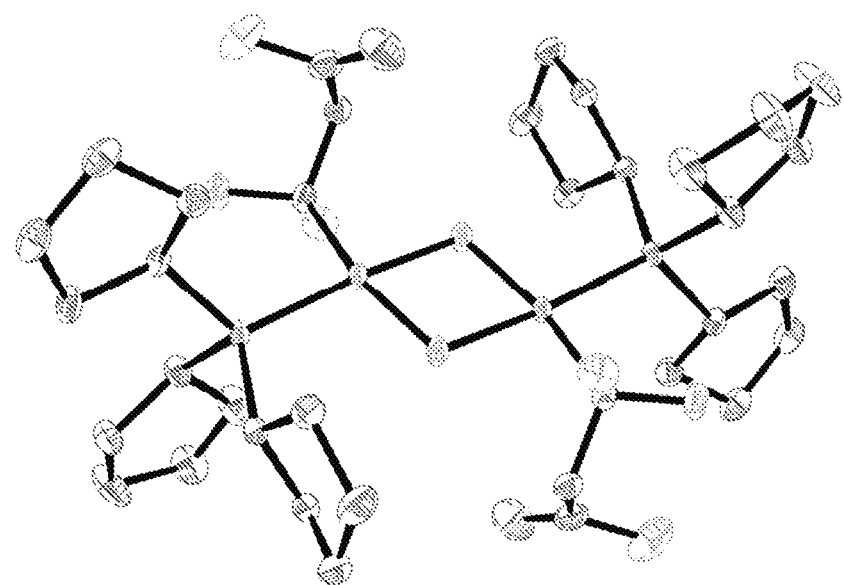

This application is a divisional application of U.S. Ser. No. 16/329,603 filed Feb. 28, 2019, which is the National Phase of and claims priority from, International Patent Application Number PCT/CA2017/051023 filed Aug. 30, 2017, which claims priority from U.S. Provisional Application Ser. No. 62/381,841 filed Aug. 31, 2016, each of which is incorporated herein by reference.

FIELD OF THE INVENTION

The present application pertains to the field of fluoroolefins. More particularly, the present application relates to a catalytic process for manufacture of fluoroolefins, and products thereof.

INTRODUCTION

Fluorocarbon based fluids have found widespread use in many commercial and industrial applications. For example, fluorocarbon based fluids are frequently used as working fluids in systems such as air conditioning, heat pump and refrigeration applications.

Certain fluorocarbons have been a preferred component in many heat exchange fluids, such as refrigerants, for many years in many applications. For, example, fluoroalkanes, such as chlorofluoromethane and chlorofluoroethane derivatives, have gained widespread use as refrigerants in applications including air conditioning and heat pump applications owing to their unique combination of chemical and physical properties.

Concern has increased in recent years about potential damage to the earth's atmosphere and climate, and certain chlorine-based compounds have been identified as particularly problematic in this regard. The use of chlorine-containing compositions (such as chlorofluorocarbons (CFCs), hydrochlorofluorocarbons (HCFCs) and the like) as refrigerants in air-conditioning and refrigeration systems has become disfavored because of the ozone-depleting properties associated with many of such compounds. There has thus been an increasing need for new fluorocarbon and hydrofluorocarbon compounds and compositions that offer alternatives for refrigeration and heat pump applications.

It is generally considered important, however, that any potential substitute refrigerant also possess those properties present in many of the most widely used fluids, such as excellent heat transfer properties, chemical stability, low- or no-toxicity, non-flammability and lubricant compatibility, among others. Hydrofluoroolefins ("HFOs") and hydrochlorofluoroolefins ("HCFOs") have been found to have particular value as substitute refrigerant compounds and are sometimes referred to as "fourth generation" refrigerants. Typically these compounds have approximately a thousand time lower global warming potential ("GWP") than hydrofluorocarbons (HFCs). HFO and HCFO models currently in use include 2,3,3,3-tetrafluoropropene (HFO-1234yf), 1,3,3,3-tetrafluoropropene (HFO-1234ze), and 1-Chloro-3,3,3-trifluoropropene (HCFO-1233zd).

However, to date, there is no efficient process that minimizes environmental toxicity for the synthesis of such compounds.

The current state of the art comprises many examples in which target hydrofluoroölefins are obtained by replacing a C—X bond (X being a heteroatom other than fluorine) with a C—F bond using hydrofluoric acid as the fluoride source, and a Lewis acid (either heterogeneous or homogeneous) as the catalyst. These conditions are well known to skilled practitioners in the art, and are frequently referred to as Swarts Reactions in reference to their original inventor. The olefinic functionality is introduced most commonly by either thermal or alkaline dehydrohalogenation of saturated hydrofluorocarbons or hydrochlorofluorocarbons.

In U.S. Pat. No. 6,242,658 Baker et al describe a nickel-catalyzed hydrodimerization reaction of two tetrafluoroethylene equivalents to give a nickelacyclopentane, which can undergo hydrogenolysis to give the saturated four-carbon product: 1H,4H-octafluorobutane (HFC-338pcc). In U.S. Pat. No. 9,315,431, Pigamo et al. describe a process wherein hydrochloroolefins (HCOs)—olefins bearing at least one C—H and C—Cl bond—are converted to HFOs and hydrochlorofluoroölefins (HCFOs)—olefins bearing at least one C—H, C—Cl, and C—F bond—by fluorination with HF in the liquid phase using an R-122 admixture with imidazolium ionic liquid as the solvent. In this process, the chlorine is lost as HCl and is subsequently removed from the reaction mixture by distillation. U.S. Pat. No. 8,895,788 (Elsheikh et al.) dislcoses a preparation of HCFO-1233xf wherein HCC-240fa undergoes several dehydrochlorination steps, followed by eventual fluorination to HFO-1234yf using a similar strategy. U.S. Pat. No. 8,207,384 (Wendlinger et al.) describes a production process for HFO-1234yf from HFC-243db in the gas phase using a supported chromium catalyst. U.S. patent application Ser. No. 13/695,807 (Elsheikh et al.) describes a Cr-catalyzed dehydrofluorination of hydrofluorocarbons (HFCs) to HFOs. U.S. patent application Ser. No. 13/642,589 (Pigamo et al.) describes a fluorination using HF in ionic liquid where HCFO-1233xf may be prepared from either HCC-240db or HCC-240aa. U.S. Pat. No. 9,278,895 (Deur-Bert et al.) discloses a manufacturing process for the same reaction in the gas phase using a supported Cr catalyst. U.S. Pat. No. 9,302,961 (Pigamo et al.) describes a high-temperature (350° C.) fluorination using a catalyst comprised of a supported mixture of Ni and Cr where HFO-1234yf may be prepared from HCC-240aa, HCFC-243db, HCO-1230xf, or HCFO-1233xf. U.S. patent application Ser. No. 12/770,217 (Cook et al.) describes an elimination reaction of HCFC-235fa to HFO-1225zc in aqueous alkaline media. U.S. Pat. No. 8,288,597 (Mallikarjuna, Sievert, & Nappa) describes the dehydrofluorination of HFC-236ea to HFO-1225ye in a solvent mixture using a phase-transfer catalyst.

Very few $C_4$—HFOs are in current use, with the most popular being 1,1,1,4,4,4-hexafluoro-2-butylene (HFO-1336mzz), which can be prepared by heating HCFO-1233xf to between 600-650° C. over a $Fe_2O_3/NiO$ catalyst, as described in U.S. Pat. No. 9,353,030 (Nair et al.). Some $C_4$—HCFOs are also known in the art; for example, 2-chloro and 2,3-dichloro-1,1,1,4,4,4-hexafluoro-2-butylene has been prepared according to the process disclosed in U.S. Pat. No. 5,969,197 (Lui et al.) that includes fluorination of 1,1,2,3,3,4,4-heptachlorobutylene with HF over a Cr catalyst. 1,3,4,4,4-pentafluoro-3-trifluoromethyl-1-butylene (HFO-1438ezy) has been prepared from 1,4-dibromo-1,1,2,4-tetrafluoro-2-trifluoromethyl-butane in several steps as developed by Jackson et al. in US Patent Application No. 20160046547 A1.

A need remains for an efficient process for synthesis of hydrofluoroölefins.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide a process for catalytic hydrodefluorodimerization of fluoroolefins in the liquid phase. In accordance with an aspect of the present application, there is provided a process for preparing a hydrofluoroolefin of Formula II

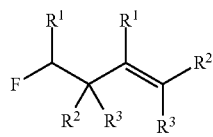

comprising:
treating a compound of Formula I with a hydride source, a ligand and nickel[0] catalyst

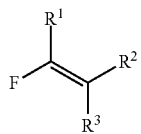

where $R^1$, $R^2$ and $R^3$ are each independently H, F, $R^F$, n-alkyl, isoalkyl, tert-alkyl, cycloalkyl, aryl, alkenyl, $NR_2$, OR, SR, or $R_3Si$, where R is an n-alkyl, isoalkyl, tert-alkyl, cycloalkyl, aryl, or alkenyl.

In accordance with another aspect of the present application, there is provided a compound of Formula III

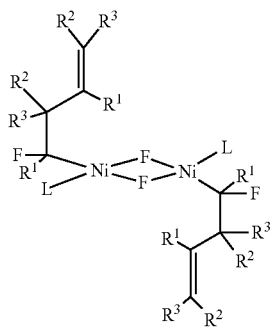

where $R^1$, $R^2$ and $R^3$ are each independently H, F, $R^F$, n-alkyl, isoalkyl, tert-alkyl, cycloalkyl, aryl, alkenyl, $NR_2$, OR, SR, or $R_3Si$ where R is an n-alkyl, isoalkyl, tert-alkyl, cycloalkyl, aryl, or alkenyl.

In accordance with another aspect of the application, there is provided a liquid composition comprising a fluoroolefin manufactured by a process employing a zerovalent nickel catalyst as described herein.

BRIEF DESCRIPTION OF TABLES AND FIGURES

Figure 2:
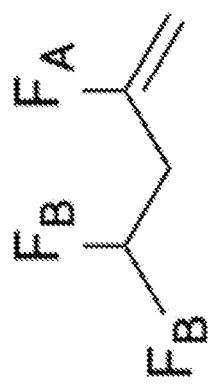
Figure 2:
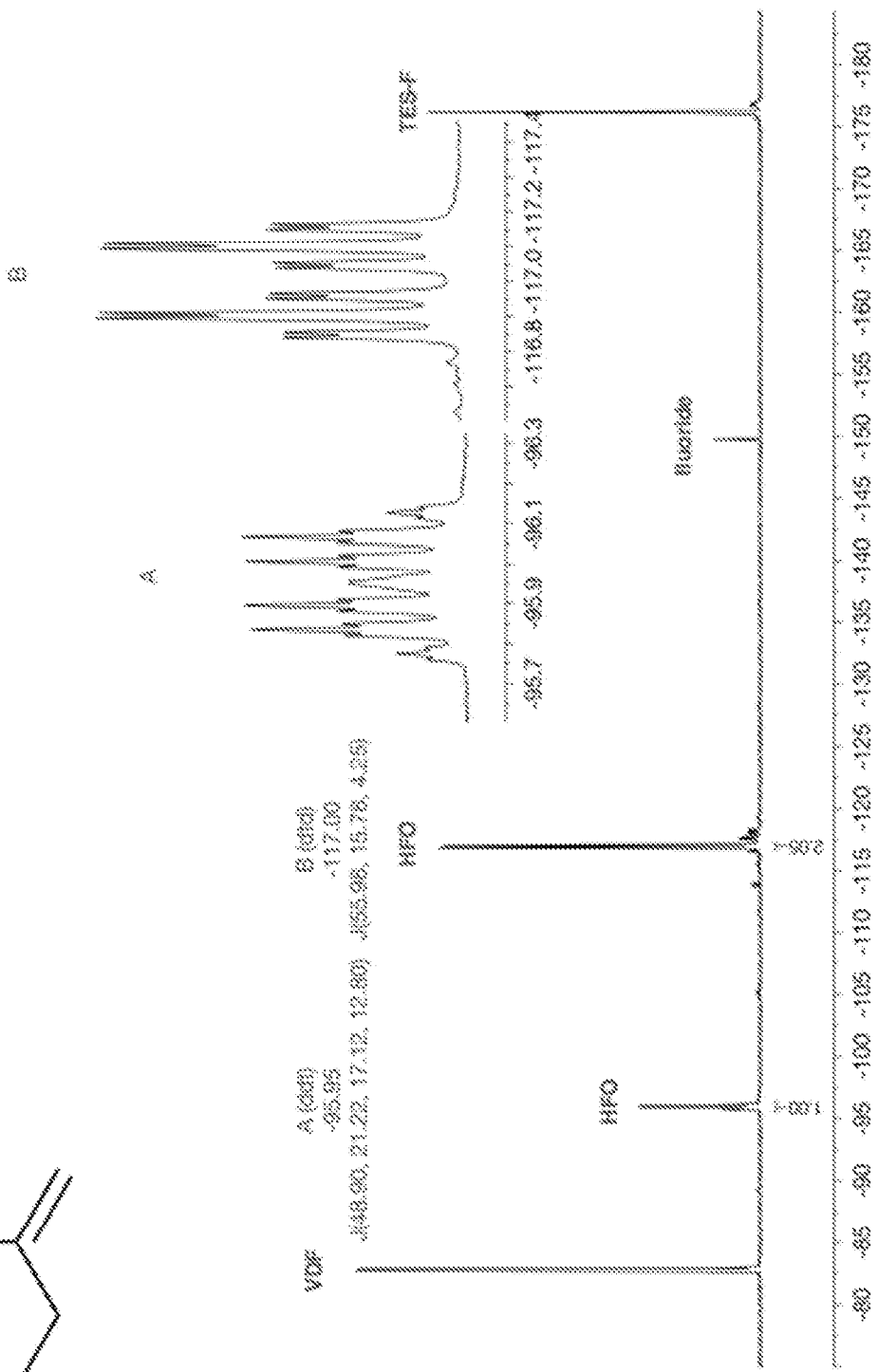

For a better understanding of the application as described herein, as well as other aspects and further features thereof, reference is made to the following description which is to be used in conjunction with the accompanying drawings, where:

FIG. 1 depicts an ORTEP diagram of the μ-F dimer with tricyclopentylphosphine as the ligand; and FIG. 2 depicts a $^{19}F$ NMR spectrum (at 292 MHz) of the reaction performed in Example 1.

DETAILED DESCRIPTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "alkyl" as a group or part of a group means a straight chain or, where available, a branched chain alkyl moiety or a cyclic alkyl moiety. For example, it may represent a C1-12 alkyl function or a C1-4 alkyl function, as represented by methyl, ethyl, n-propyl, i-propyl, n-butyl, s-butyl and t-butyl.

The term "alkenyl" as used herein includes straight-chained, branched and cyclic alkenyl groups, such as vinyl and allyl, groups.

The term "halogen" herein means a fluorine, chlorine, bromine or iodine atom.

The term "fluoroalkyl", or "$R^F$", is used herein to refer to an alkyl in which one or more hydrogen has been replaced with a fluorine.

As used herein, the term "hydrofluoroolefin" refers to compounds composed of hydrogen, fluorine, and carbon, that are derivatives of alkenes.

The present application provides a hydrodefluorodimerization process, which is useful in the synthesis of, for example, fluoroolefins that can be used as refrigerants, blowers and the like. Previous methods for synthesis of such hydrofluoroölefins are typically expensive, time consuming and/or they involve the use of hazardous or environmentally damaging chemicals. In contrast, the present method makes no use of HF or caustic alkali (which feature prominently in currently used processes). The present method is an "early-stage fluorination" process, wherein precursors containing fluorine are assembled into the desired product. This differs from the "late-stage fluorination" strategy more frequently employed in the current art, where precursors are assembled containing C—Cl bonds that are later converted to C—F bonds. A separate dehydrofluorination step using caustic acid is also frequently employed to obtain alkeneic functionality. Again, this step is avoided using the presently provided hydrodefluorodimerization process.

The hydrodefluorodimerization process is summarized in Scheme 1, where a starting compound of Formula I is dimerized by reaction with a nickel catalyst, to form a compound of Formula II:

Scheme 1

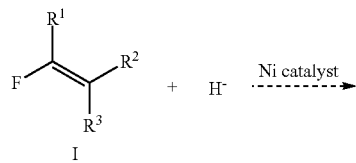

where $R^1$, $R^2$ and $R^3$ are each independently H, F, $R^F$ (or fluoroalkyl), n-alkyl (where an "alkyl" is, for example, $C_1$-$C_{20}$ alkyl, $C_1$-$C_{12}$ alkyl or $C_1$-$C_6$ alkyl), isoalkyl, tert-alkyl, cycloalkyl (for example, having a ring size between 4 and 8 carbons), aryl, alkenyl, $NR_2$, OR, SR, or $R_3Si$, where where R is an n-alkyl, isoalkyl, tert-alkyl, cycloalkyl, aryl, or alkenyl.

In one example, the hydride source is a silane and the reaction proceeds as shown in Scheme 2:

Scheme 2

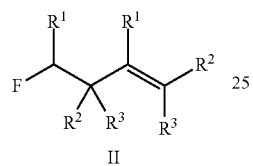

where R' is n-alkyl, isoalkyl, cycloalkyl, aryl, alkenyl, $NR_2$, OR, or $R_3Si$.

In an alternative example, the hydride source is $H_2$ and a weak, preferably insoluble, non-nucleophilic base (e.g., an alkali metal carbonate or phosphate) in order to rapidly quench the resulting hydrofluoric acid.

The process is a catalytic process wherein a source of zerovalent nickel and one molar equivalent of a neutral ligand in a solvent (the precatalyst mixture) is subjected to a feed containing a fluoroalkene of Formula I, or a blend of fluoroalkenes of Formula I. In accordance with certain specific embodiments, the fluoroalkene is vinylidene difluoride, trifluoroethylene (HFO-1123), vinyl fluoride (HFO-1141), 2,3,3,3-trifluoropropylene (HFO-1234yf), and 1,3,3,3-trifluoropropylene (HFO-1234ze), or any combination thereof.

The zerovalent nickel catalyst can be used directly or generated in situ from a divalent nickel salt and a suitable reducing agent, such as, but not limited to, nickel bis(pivalate) and triethylsilane with the IAd ligand. Alternatively, the nickel catalyst already exists as nickel(0), such as, but not limited to, nickel bis(1,5-cyclooctadiene). The neutral ligand employed can be, for example, a phosphine ligand or an N-heterocyclic carbene ligand, for example, as shown below:

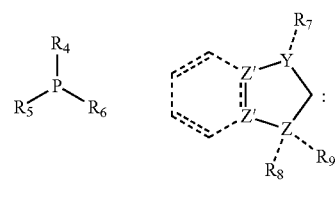

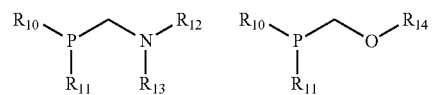

wherein each of $R^4$-$R^9$ is independently n-alkyl, iso-alkyl, ter-alkyl, cycloalkyl, aryl, silyl, or dialkylamino;

each of $R^{10}$ and $R^{11}$ is independently n-alkyl, iso-alkyl, ter-alkyl, cycloalkyl, aryl, silyl, dialkylamino, or (alkylamino)methyl;

each of $R^{12}$ and $R^{13}$ is independently n-alkyl, iso-alkyl, ter-alkyl, cycloalkyl, aryl, silyl, or a hydrogen atom;

$R^{14}$ is independently n-alkyl, iso-alkyl, ter-alkyl, cycloalkyl, aryl, silyl, or a hydrogen atom;

Z is O, S, $N(R^8)$ or $CR^8R^9$;

each Z' is independently N or C, and wherein dashed lines represent optional bonds.

In one embodiment, the silane is nonvolatile to facilitate the separation of the gaseous product stream from the reaction mixture.

Without wishing to be bound by theory, it is proposed that the reaction proceeds according to the reaction pathway shown in Scheme 3:

Scheme 3

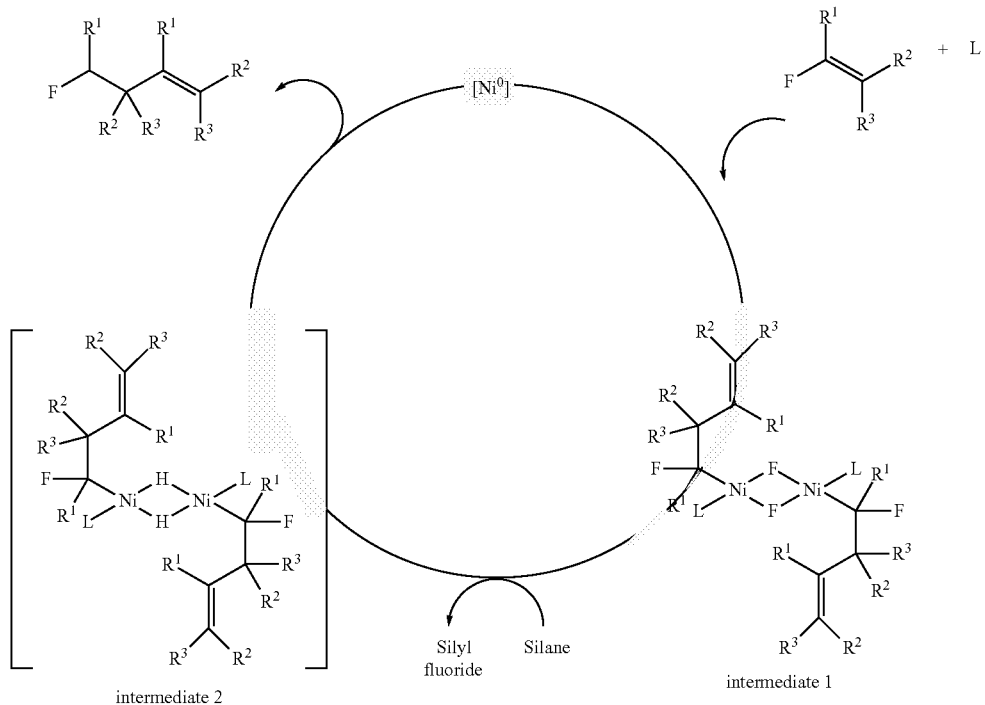

When the μF dimer is contacted with a silane reagent, the F in intermediate 1 is replaced with H, which leads to spontaneous reductive elimination to the hydrofluoroolefin of interest and regeneration of the zerovalent nickel catalyst.

In one example, the hydrodefluorodimerization process is used to manufacture 2,4,4-trifluorobut-1-ene (HFO-1363pyf), as shown in Scheme 4, and as further described in Example 1 below:

Scheme 4

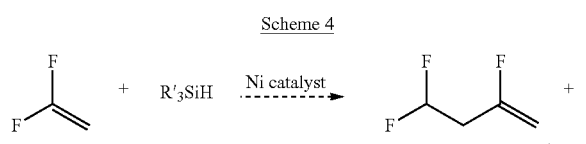

where R' is as defined above.

Two additional examples of the hydrodefluorodimerization process used to manufacture fluoroolefins are provided below:

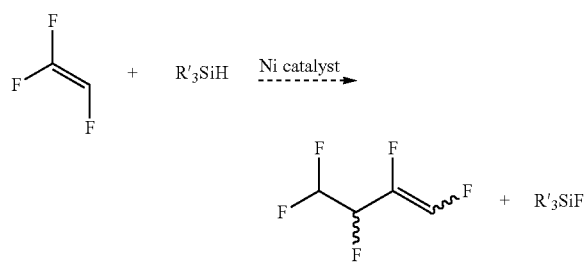

-continued

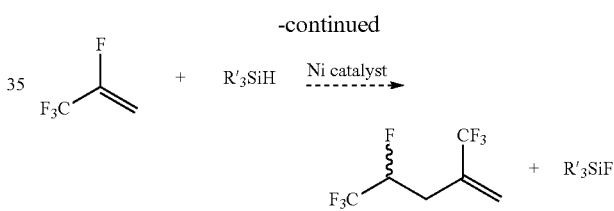

where R' is as defined above.

Both of these examples are useful for producing compounds having utility as, for example, refrigerants and/or blowing agents.

The process provided herein can also be used to manufacture hydrochlorofluoroölefins (HCFOs), which is another class of low GWP refrigerants and blowing agents.

Catalytic Reaction Process

The reaction is preferably carried out in a solvent of high boiling point (preferably between 80-300° C., most advantageously between 110-200° C.), and having sufficient polarity to dissolve the precatalyst mixture such that the reaction is fully homogeneous. The solvent should be stable in a reducing environment [including nickel(0)]. Examples of preferred solvents include xylenes (either ortho-, meta-, para-, or mixtures thereof), mesitylene, tert-butyltoluene, and other high-boiling aromatic hydrocarbons. Aliphatic solvents such as isooctane or n-decane may also be used.

External heat can be applied to the reaction, in which case functional reaction temperatures depend on the nature of the neutral ligand applied (viz. its ability to stabilize the zerovalent nickel intermediate off-cycle). The preferred temperature range is between 25-150° C., and most advantageously 45-110° C.

The volatile product(s) of the reaction can be separated from the reaction medium by vacuum distillation and, if necessary, subjected to further cryogenic distillation to produce the target HFOs in their pure form.

In a specific embodiment, the reaction is performed using tert-butyltoluene as the solvent, triethylsilane as the silane, and a reaction temperature between 45-65° C. The ratio of solvent to silane is between 3:1 and 1:1 (v/v). The nickel catalyst, formed by combining bis(1,5-cyclooctadiene)nickel(0) and a suitable phosphine ligand in a 1:1 ratio, can be loaded at between 1-10 mol %, most advantageously (and economically) at 1 mol %. The ligand employed is preferably a phosphine ligand, most advantageously tricyclopentylphosphine or di(tert-butyl)(n-alkyl)phosphine derivatives.

Compositions

The present application also provides compositions comprising a $C_{4-8}$ fluoroölefin produced by a process comprising dimerization of a $C_2$-$C_4$ fluoroalkene in the presence of a nickel(0) catalyst and a silane.

In certain examples, compositions of the present application have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

In certain examples, the present compositions also have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the hydrofluoroolefin compounds, such as, for example HFO-1363pyf, contained in the present compositions can vary widely, depending the particular application, and compositions containing more than trace amounts and less than 100% of the compound are within broad the scope of the present application. Moreover, the compositions of the present application can be azeotropic, azeotrope-like or non-azeotropic. In certain examples, the present compositions comprise a hydrofluoroolefin manufactured by the present method, for example HFO-1363pyf, in amounts from about 5% by weight to about 99% by weight, or from about 5% to about 95%. Many additional compounds can be included in the present compositions. In certain embodiments, the present compositions include more than one HFO, or a mixture of one or more HFO with one or more HCFO, or one or more HFC, or both.

The relative amount of any of the above noted components, as well as any additional components (e.g., water or $CO_2$) that may be included in present compositions, can vary widely within the general broad scope of the present invention according to the particular application for the composition, and all such relative amounts are considered to be within the scope hereof.

To gain a better understanding of the invention described herein, the following examples are set forth. It should be understood that these examples are for illustrative purposes only. Therefore, they should not limit the scope of this invention in any way.

EXAMPLES

Example 1: Synthesis of HFO-1363pyf

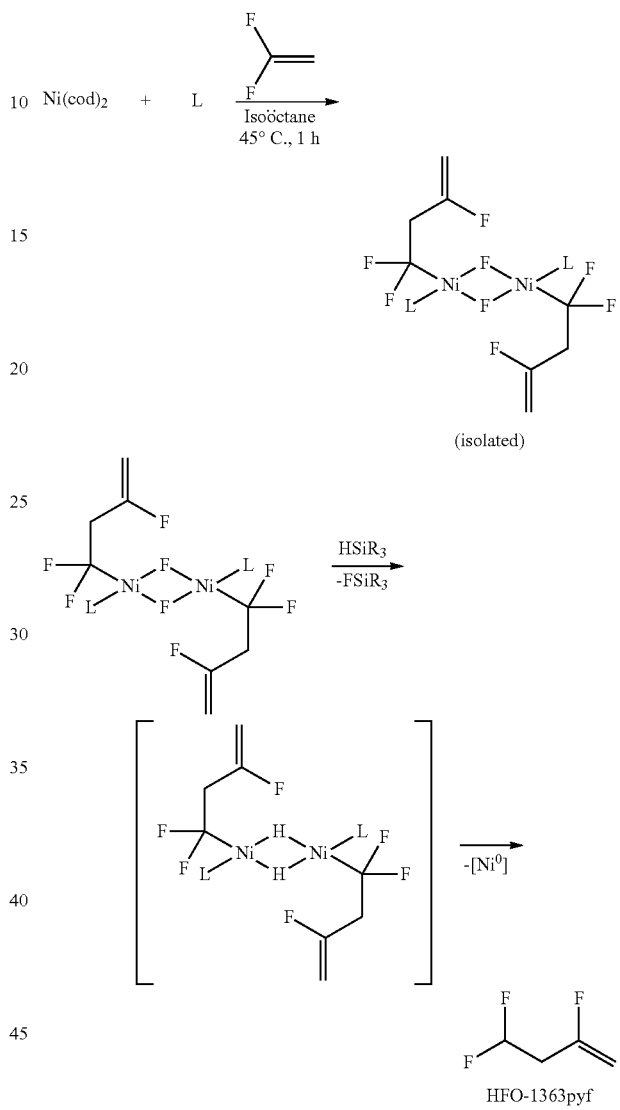

The scheme shown above outlines the process used to manufacture HFO-1363pyf. As depicted, the μ-F dimer generated from reaction of vinylidene difluoride with the nickel catalyst and ligand, was subjected to a silane reagent. The silane reagent replaced F with H leading to spontaneous reductive elimination to HFO-1363pyf, the C4 hydrofluoroolefin of interest. The μ-F dimers were easily isolated in >70% yield when L was an N-heterocyclic carbene (NHC) ligand, namely 1-adamantyl (IAd) or 1-tert-butyl (ItBu) substituted NHCs.

It was determined that the solvent could be anything in which bis(1,5-cyclooctadiene)nickel(0) and the ligand of choice are stable, but isooctane was preferred due to the low solubility of the product in the medium, and the higher product yield obtained compared to other solvents. Pure solutions containing the dimer with bulky phosphine ligands were also prepared, but due to the oily physical property of the phosphine ligands attempted, isolation of pure solid material (devoid of any remaining phosphine or nickel(0)) was more difficult than when using the NHC ligands. Tricyclopentylphosphine and di(tert-butyl)n-butylphosphine have been used successfully to this end, and have been characterized by $^{19}F$ and $^{31}P$ NMR. Smaller phosphines (e.g., tributylphosphine or tripropylphosphine) were attempted with no observation of the μ-F dimer. Crystal structures of complexes containing L=IAd, and L=tricyclopentylphosphine have also been obtained. FIG. 1 depicts an ORTEP diagram of the μ-F dimer with tricyclopentylphosphine as the ligand.

An exemplary synthesis for the complex where L=1-adamantyl is detailed further below:

IAd (61 mg, 0.182 mmol) and bis(1,5-cycloöctadiene)nickel(0) (50 mg, 1 eq.) were added to a scintillation vial and dissolved in anhydrous isooctane (5 ml). The vial was sealed with a septum-fitted screw cap and vinylidene difluoride (50 ml) was added via syringe injection directly to the solution. The solution was allowed to stir at 45° C. for 1 hour, after which time a tangerine-orange precipitate formed. The vial was then cooled to -35° C. and filtered through a medium porosity fritted glass funnel to give the product as a golden-yellow powder which was dried in vacuo (75 mg, 79% yield).

$^{1}H$ NMR (400 MHz): 6.41 ppm (2H s, NHC backbone), 4.55 ppm (1H dd, 17, 2.2 Hz, =CH cis), 4.16 ppm (1H dd, 49, 2.2 Hz, =CH trans), 3.65 ppm (6H d(b), Ad CH$_2$), 3.30 ppm (6H d(b), Ad CH$_2$), 3.20 ppm (2H q, 20 Hz, CF$_2$CH$_2$—CF=), 2.50 ppm (6H, s(b), Ad CH), 2.15 ppm (6H d(b), Ad CH$_2$), 1.90 ppm (6H, d(b), Ad CH$_2$). $^{19}F$ NMR (376 MHz): -71.1 ppm (2F qt, 20, 12, 7 Hz, α-CF$_2$), -87.3 ppm (1F dq, 49, 17, 7 Hz, γ-CF), -426.7 ppm (Ni—F).

The solvent for this reaction was preferably isooctane (for highest yield) but methyl tert-butyl ether was also used, with moderate effectiveness.

The product was soluble in THF, and aromatic solvents, and thus if any of these solvents are used as the preparative medium, the volatiles must be first removed under reduced pressure during workup, and the residue triturated with hexanes to liberate the product. X-ray quality crystals were obtained from a warm toluene liquor.

An exemplary synthesis for the complex where L=tricyclopentylphosphine is detailed further below:

A mixture was made comprising 0.2 ml of triethylsilane and 0.4 ml of xylenes in an NMR tube. To this mixture was added bis(1,5-cyclooctadiene)nickel(0) (3 mg, 0.012 mmol) and tricyclopentylphosphine (3 mg, 0.012 mmol). The resulting precatalytic mixture was sealed with a septum-cap, subjected to 3 ml of vinylidene difluoride by syringe injection, and placed in a 45° C. silicone oil bath filled at least to the solvent line of the tube. A $^{19}F$ NMR was taken after 45 minutes, which showed the presence HFO-1363pyf, triethylsilyl fluoride, free fluoride, and unreacted vinylidene difluoride (see FIG. 2).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A compound of Formula III

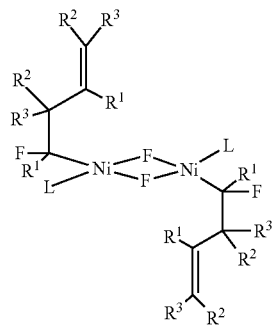

where $R^1$, $R^2$ and $R^3$ are each independently H, F, $R^F$, n-alkyl, iso-alkyl, tert-alkyl, cycloalkyl, aryl, alkenyl, NR$_2$, OR, SR, or R$_3$Si where R is an n-alkyl, iso-alkyl, tert-alkyl, cycloalkyl, aryl, or alkenyl; and L is a ligand.

2. A liquid composition comprising a fluoroölefin of Formula III

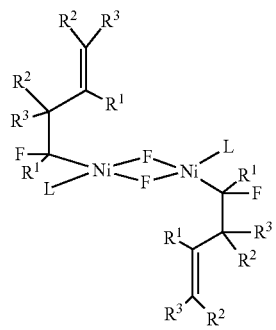

where $R^1$, $R^2$ and $R^3$ are each independently H, F, $R^F$, n-alkyl, iso-alkyl, tert-alkyl, cycloalkyl, aryl, alkenyl, NR$_2$, OR, SR, or R$_3$Si where R is an n-alkyl, iso-alkyl, tert-alkyl, cycloalkyl, aryl, or alkenyl; and L is a ligand.

3. The composition of claim 2, wherein the fluoroölefin is present at an amount of from about 5% by weight to about 99% by weight, or from about 5% to about 95%.

4. The composition of claim 2, wherein the composition is azeotropic or azeotrope-like.

5. The composition of claim 2, wherein the composition is non-azeotropic.

6. The composition of claim 2, wherein the composition additionally comprises water and/or CO$_2$.

7. The composition of claim 2, wherein the composition additionally comprises one or more additional fluoroölefin, hydrochlorofluoroölefin, hydrofluorocarbon, or a combination thereof.

8. The compound of claim 1, wherein L is a phosphine or an N-heterocyclic carbine.

9. The compound of claim 1, wherein L is a compound of Formula IV, V, VI, or VII,

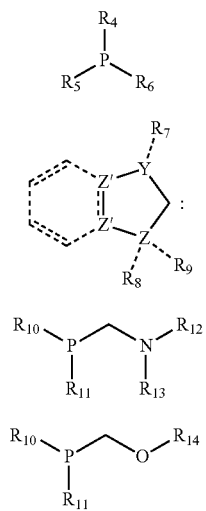
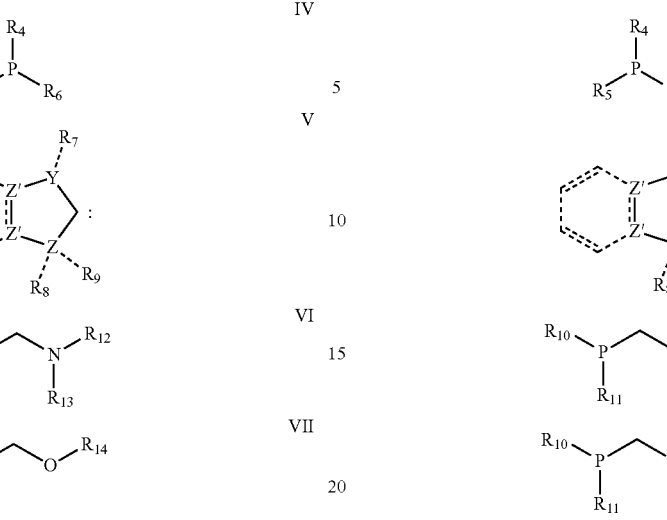

wherein each of $R^4$-$R^9$ is independently n-alkyl, iso-alkyl, tert-alkyl, cycloalkyl, aryl, silyl, or dialkylamino;

each of $R^{10}$ and $R^{11}$ is independently n-alkyl, iso-alkyl, tert-alkyl, cycloalkyl, aryl, silyl, dialkylamino, or (alkylamino)methyl;

each of $R^{12}$ and $R^{13}$ is independently n-alkyl, iso-alkyl, tert-alkyl, cycloalkyl, aryl, silyl, or a hydrogen atom;

$R^{14}$ is independently n-alkyl, iso-alkyl, tert-alkyl, cycloalkyl, aryl, silyl, or a hydrogen atom;

Z is O, S, N($R^8$) or $CR^8R^9$;

each Z' is independently N or C, and wherein dashed lines represent optional bonds.

10. The composition of claim 2, wherein L is a phosphine or an N-heterocyclic carbine.

11. The composition of claim 2, wherein L is a compound of Formula IV, V, VI, or VII, wherein each of $R^4$-$R^9$ is independently n-alkyl, iso-alkyl, tert-alkyl, cycloalkyl, aryl, silyl, or dialkylamino;

each of $R^{10}$ and $R^{11}$ is independently n-alkyl, iso-alkyl, tert-alkyl, cycloalkyl, aryl, silyl, dialkylamino, or (alkylamino)methyl;

each of $R^{12}$ and $R^{13}$ is independently n-alkyl, iso-alkyl, tert-alkyl, cycloalkyl, aryl, silyl, or a hydrogen atom;

$R^{14}$ is independently n-alkyl, iso-alkyl, tert-alkyl, cycloalkyl, aryl, silyl, or a hydrogen atom;

Z is O, S, N($R^8$) or $CR^8R^9$;

each Z' is independently N or C, and wherein dashed lines represent optional bonds.

* * * * *